United States Patent
Onuma et al.

(10) Patent No.: US 9,867,673 B2
(45) Date of Patent: Jan. 16, 2018

(54) MEDICAL SUPPORT DEVICE

(71) Applicants: Canon U.S.A., Inc., Melville, NY (US); The Brigham and Women's Hospital Inc., Boston, MA (US)

(72) Inventors: Kazufumi Onuma, Kawasaki (JP); Takahisa Kato, Brookline, MA (US); Nobuhiko Hata, Newton, MA (US); Kemal Tuncali, Newton, MA (US); Brian Ninni, Somerville, MA (US); Peter Tia, Dracut, MA (US)

(73) Assignees: Canon U.S.A, Inc., Melville, NY (US); The Brigham and Women's Hospital, Inc., Boston, MA (US)

( * ) Notice: Subject to any disclaimer, the term of this patent is extended or adjusted under 35 U.S.C. 154(b) by 21 days.

(21) Appl. No.: 14/799,021

(22) Filed: Jul. 14, 2015

(65) Prior Publication Data
US 2017/0014200 A1    Jan. 19, 2017

(51) Int. Cl.
*A61B 19/00* (2006.01)
*A61B 90/11* (2016.01)
(Continued)

(52) U.S. Cl.
CPC .......... *A61B 90/11* (2016.02); *A61B 17/3403* (2013.01); *A61B 90/94* (2016.02);
(Continued)

(58) Field of Classification Search
CPC ................ A61B 90/11; A61B 17/3403; A61B 2017/3407; A61B 2017/3403; A61M 25/06
See application file for complete search history.

(56) References Cited

U.S. PATENT DOCUMENTS

| 4,608,977 A | 9/1986 | Brown |
| 4,841,967 A | 6/1989 | Chang et al. |

(Continued)

FOREIGN PATENT DOCUMENTS

| CA | 2784988 A1 | 2/2013 |
| CN | 201108500 Y | 9/2008 |

(Continued)

OTHER PUBLICATIONS

Koethe, Y., et al., "Accuracy and efficacy of percutaneous biopsy and ablation using robotic assistance under computed tomography guidance: a phantom study" Eur Radiol., 2013.
(Continued)

*Primary Examiner* — Robert N Wieland
(74) *Attorney, Agent, or Firm* — Canon U.S.A, Inc. IP Division

(57) ABSTRACT

There is provided a medical support device for holding and positioning a needle. This device is particularly useful for positioning needles in a less invasive puncture treatment. This device comprises two rotational elements and at least one needle guide attached to a rotational element and. The needle guide guides the direction of insertion of a needle-like instrument and includes a guide portion that guides a needle or other needle-like instrument where the puncture point of the needle in a first position is different from the puncture point when the needle guide guides the needle in a second position.

18 Claims, 11 Drawing Sheets

(51) Int. Cl.
  *A61B 17/34* (2006.01)
  *A61B 17/00* (2006.01)
  *A61B 90/94* (2016.01)
(52) U.S. Cl.
  CPC .............. *A61B 2017/00398* (2013.01); *A61B 2017/3407* (2013.01)

(56) References Cited

U.S. PATENT DOCUMENTS

| | | | |
|---|---|---|---|
| 5,196,019 A | 3/1993 | Davis et al. | |
| 5,201,742 A | 4/1993 | Hasson | |
| 5,280,427 A | 1/1994 | Magnusson et al. | |
| 5,682,892 A | 11/1997 | Selder et al. | |
| 5,957,934 A | 9/1999 | Rapoport | |
| 6,079,681 A | 6/2000 | Stern et al. | |
| 6,110,182 A | 8/2000 | Mowlai-Ashtiani | |
| 6,119,032 A | 9/2000 | Martin et al. | |
| 6,185,445 B1 | 2/2001 | Knuttel | |
| 6,249,713 B1 | 6/2001 | Geiger et al. | |
| 6,676,669 B2 | 1/2004 | Charles et al. | |
| 7,083,608 B2 | 8/2006 | Tomita et al. | |
| 7,187,104 B2 | 3/2007 | Yamamoto et al. | |
| 7,379,769 B2 | 5/2008 | Piron et al. | |
| 7,636,596 B2 * | 12/2009 | Solar ..................... | A61B 90/11 600/429 |
| 7,824,417 B2 | 11/2010 | Magnusson et al. | |
| 8,116,850 B2 | 2/2012 | Solar | |
| 8,241,301 B2 | 8/2012 | Zhang et al. | |
| 8,298,245 B2 | 10/2012 | Li et al. | |
| 8,308,740 B2 | 11/2012 | Tolley et al. | |
| 8,308,840 B2 | 11/2012 | Zhang et al. | |
| 2001/0000940 A1 | 5/2001 | Maruyama | |
| 2002/0019641 A1 | 2/2002 | Truwit | |
| 2003/0107299 A1 | 6/2003 | Fujimoto | |
| 2004/0064148 A1 | 4/2004 | Daum et al. | |
| 2005/0216026 A1 | 9/2005 | Culbert | |
| 2005/0261581 A1 | 11/2005 | Hughes et al. | |
| 2006/0149147 A1 | 7/2006 | Yanof | |
| 2006/0229641 A1 | 10/2006 | Gupta et al. | |
| 2007/0276407 A1 | 11/2007 | Vogele | |
| 2008/0004481 A1 | 1/2008 | Bax et al. | |
| 2008/0161829 A1 | 7/2008 | Kang | |
| 2008/0167663 A1 | 7/2008 | De Mathelin et al. | |
| 2008/0200798 A1 | 8/2008 | Eklund et al. | |
| 2009/0079431 A1 | 3/2009 | Piferi et al. | |
| 2009/0234369 A1 | 9/2009 | Bax et al. | |
| 2010/0010505 A1 | 1/2010 | Herlihy et al. | |
| 2010/0082040 A1 | 4/2010 | Sahni | |
| 2011/0190787 A1 | 8/2011 | Sahni | |
| 2011/0237881 A1 | 9/2011 | Kunz | |
| 2011/0251624 A1 | 10/2011 | Yi et al. | |
| 2012/0022368 A1 | 1/2012 | Brabrand et al. | |
| 2013/0066192 A1 | 3/2013 | Sarvestani et al. | |
| 2013/0069651 A1 | 3/2013 | Luminani | |
| 2013/0345718 A1 | 12/2013 | Crawford et al. | |
| 2014/0052154 A1 | 2/2014 | Griffiths et al. | |
| 2014/0121675 A1 | 5/2014 | Bax et al. | |
| 2014/0128881 A1 | 5/2014 | Tyc | |
| 2014/0128883 A1 | 5/2014 | Piron et al. | |
| 2014/0200445 A1 | 7/2014 | Boezaart et al. | |
| 2014/0275978 A1 | 9/2014 | Fujimoto et al. | |
| 2014/0275979 A1 | 9/2014 | Fujimoto et al. | |
| 2014/0336670 A1 | 11/2014 | Brabrand et al. | |
| 2014/0350572 A1 | 11/2014 | Elhawary et al. | |
| 2015/0238266 A1 | 8/2015 | Fujimoto et al. | |
| 2016/0074063 A1 | 3/2016 | Arimitsu et al. | |
| 2017/0030557 A1 | 2/2017 | Chen et al. | |
| 2017/0071626 A1 | 3/2017 | Onuma et al. | |

FOREIGN PATENT DOCUMENTS

| | | |
|---|---|---|
| EP | 2561821 A1 | 2/2013 |
| JP | 2004320846 A | 11/2004 |
| JP | 2005083961 A | 3/2005 |
| JP | 2008237971 A | 10/2008 |
| WO | 2011082517 A1 | 7/2011 |
| WO | 2011082518 A1 | 7/2011 |
| WO | 2012178109 A1 | 12/2012 |
| WO | 2013084107 A2 | 6/2013 |
| WO | 2014122685 A1 | 9/2014 |
| WO | 2017/132505 A1 | 8/2017 |

OTHER PUBLICATIONS

Maxio Brochure: Planning and Targeting for CT guided Procedures by Perfint.
Palmer, K., et al, "Development and evaluation of optical needle depth sensor for percutaneous diagnosis and therapies", Medical Imaging, Proc of SPIE, 2014, vol. 9036.
Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, Tokyo, Japan.
Hata, H., et al.,"MRI-Compatible Manipulator With Remote-Center-of-Motion Control", J Magn Reson Imaging, May 2008, 27(5): 1130.
Perfint, Inc Maxio Robot—Features http://www.perfinthealthcare.com/MaxioFeatures.asp Accessed Sep. 11, 2015.
Fischer, G. S.,et al., "MRI Guided Needle Insertion—Comparison of Four Technique" In Annual Scientific Conference of the Society of Interventional Radiology, 2006. (Abstract Only).
Song, S.F., et al., "Design Evaluation of a Double Ring RCM Mechanism for Robotic Needle Guidance in MRI-guided Liver Interventions", International Conference on Intelligent Robots and Systems, Nov. 3-7, 2013, Tokyo, Japan.
Song, S.F., et al., "Biopsy Needle Artifact Localization in MRI-guided Robotic Transrectal Prostate Intervention", IEEE Trans. Biomed Eng., Jul. 2012, 59(7), pp. 1902-1911.
U.S. Office Action issue in U.S. Appl. No. 13/836,708 dated Jan. 11, 2017.
U.S. Office Action issue in U.S. Appl. No. 13/836,708 dated Jun. 27, 2017.
U.S. Office Action issue in U.S. Appl. No. 14/632,991 dated Mar. 23, 2017.

* cited by examiner

MEDICAL SUPPORT DEVICE

BACKGROUND OF THE INVENTION

Field of the Invention

The present invention relates to a medical support device for holding and positioning a needle. More specifically, the present invention relates to positioning of one or more needles in a puncture treatment.

Description of the Related Art

In medical treatment, in order to improve the QOL (quality of life) of the patient, the need for less invasive treatment is increasing. In such a situation, percutaneous puncture treatments such as percutaneous puncture ablation and percutaneous puncture cryosurgery have been developed as less invasive treatments.

However, in the case of percutaneous puncture treatment, the puncture target site is not directly visible, and therefore puncture needs to be performed on the basis of a medical image obtained using an MRI machine, a CT machine, or the like. However, since these medical imaging machines are used, an image cannot be obtained in real time. Although an image can be obtained in real time by using a special MRI machine, in that case, the work need to be performed in a narrow space. In both cases, it is difficult to precisely reach the target, and therefore the operation takes time.

In such a situation, a puncture-supporting mechanism shown in U.S. Pat. Pub. 2011/0190787 has been proposed as medical support using a medical image obtained using an MRI machine, a CT machine, or the like. According to U.S. Pat. Pub. 2011/0190787, a marker attached to a device is recognized on a medical image, and the attitude of the device is found. On the basis of this attitude and the position of the puncture target, the direction and depth of puncture may be determined and puncture is supported. In the case of this mechanism, a needle can be inserted through the same insertion point toward different puncture targets, and therefore the trauma due to puncture is minimized. In addition, the mechanism can be reduced in size, and a patient can enter an existing medical imaging machine with the device attached to them.

Operative methods performed in a state where instruments are inserted at a plurality of different target positions are increasingly used as a percutaneous puncture treatment.

However, when an operator tries to insert instruments at a plurality of different target positions, as the case of the configuration disclosed in U.S. Pat. Pub. 2011/0190787, the instruments are inserted through the same insertion point unless the installation position is changed. For this reason, when the operator tries to insert the second and subsequent instrument(s), the instruments interfere with each other, and insertion of more than one instrument cannot be performed.

In U.S. Pat. Pub. 2005/0080333, insertion of a plurality of instruments at different target positions is achieved using a grid-like positioning unit. However, a dedicated conveying bed is needed, therefore the device is large, and use in an existing imaging machine is difficult.

In view of such problems, it is desired to avoid interference between instruments with a simple mechanism. Thus, there is need for a device that can be used with multiple instruments (such as needles) where the instruments can be placed at the target sites with little to no interference between the instruments without the need to re-install the device on the patient.

SUMMARY OF THE INVENTION

A medical support device is provided that comprises: a first rotational element having a first rotation axis and a first rotational degree of freedom; a second rotational element having a second rotation axis and a second rotational degree of freedom that is attached to the first rotational element wherein the second rotation axis intersects with the first rotation axis; and at least one needle guide that is attachable to the second rotational element and is configured to guide the direction of insertion of a needle-like instrument. In this device, the at least one needle guide includes at least one guide portion that guides a first needle-like instrument through a first puncture starting point and guides a second needle-like instrument through a second puncture starting point which is different from the first puncture starting point, wherein, the at least one needle guide is in a first position when guiding the first needle-like instrument and in a second position when guiding the second needle-like instrument, or a first needle guide includes a first guide portion that guides a needle-like instrument through the first puncture starting point and a second needle guide includes a second guide portion that guides a needle-like instrument through the second puncture starting point.

Some embodiments provide a medical support device, comprising: at least one rotatable portion having at least one rotational degree of freedom and at least one needle guide attached to the rotatable portion and having a guide portion, which is configured to: (a) guide the direction of insertion of a needle-like instrument and (b) separate from the needle-like instrument after insertion of the needle-like instrument, wherein the guide portion, when the needle guide is positioned in a first position, is configured to guide the needle-like instrument to a first puncture starting point wherein the guide portion, when the needle guide is positioned in a second position, or wherein the guide portion of a second needle guide is configured to guide the needle-like instrument to a second puncture starting point which is different from the first puncture starting point.

Other embodiments provide a method comprising: attaching a medical support device to a patient, wherein the medical support device comprises a first rotational element, second rotational element, and at least two needle guides, defining at least a first location and a second location in the patient for therapeutic intervention based on an image data, attaching a first needle to a first needle guide, attaching the first needle guide to the medical support device, instructing the medical support device to rotate the first rotational element and the second rotational element to a position defined by the first location for therapeutic intervention, inserting the first needle into the patient, releasing the first needle from the medical support device, attaching a second needle to a second needle guide and attaching the second needle guide to the medical support device, instructing the medical support device to rotate the first rotational element and the second rotational element to a position defined by the second location for therapeutic intervention, inserting the second needle into the patient, wherein the second needle does not contact the first needle during insertion into the patient, and releasing the second needle from the medical support device.

BRIEF DESCRIPTION OF THE DRAWINGS

Further objects, features and advantages of the present invention will become apparent from the following detailed description when taken in conjunction with the accompanying figures showing illustrative embodiments of the present invention.

FIG. 3A is a front view. FIG. 3B is a plan view. FIG. 3C is a perspective view.

FIG. 4A is a front view. FIG. 4B is a plan view. FIG. 4C is a perspective view.

FIG. 11A is a front view. FIG. 11B is a plan view. FIG. 11C is a side view.

FIG. 12A is a front view. FIG. 12B is a plan view. FIG. 12C is a side view.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

DESCRIPTION OF THE EMBODIMENTS

First Embodiment

Configuration

A first embodiment of the present invention will be described with reference to FIG. 1 to FIG. 5B and FIG. 8B. First, the schematic configuration of a mechanical portion of a medical support device of this embodiment will be described with reference to FIG. 1.

Mechanical Configuration

Figure 1:
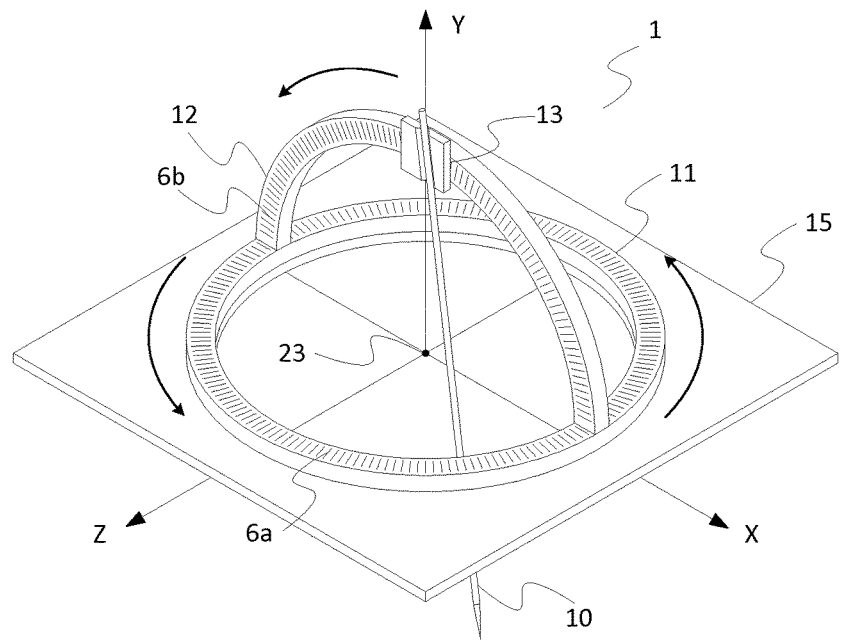
FIG. 1 shows the schematic configuration of a mechanical portion of a first embodiment.

In FIG. 1, the structure of a movable portion in each rotational element, or rotational element is omitted for simplification. First, a base 15 of a mechanical portion 1 is fixed and installed on an object to be punctured with a fixing unit (not shown).

A stationary portion of an annular, or ring shaped first rotational element 11 (also defined as a rotation mechanism) is attached to the base 15.

Figure 2:
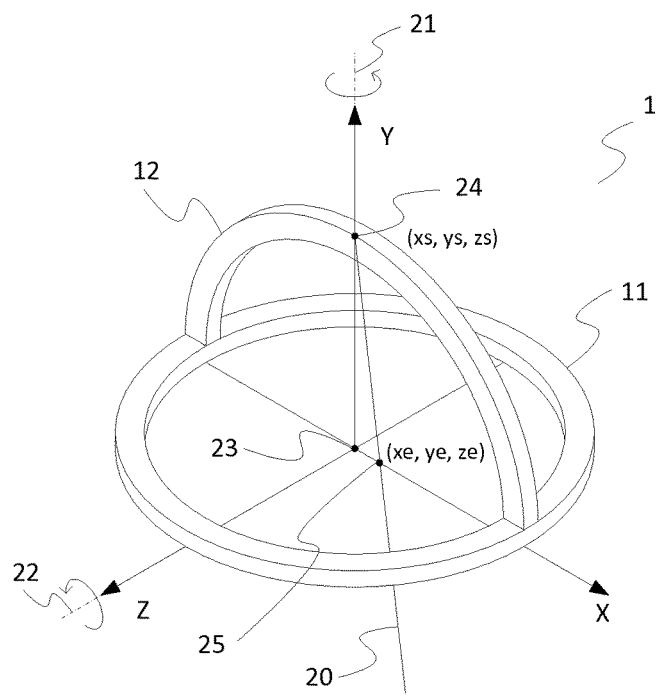
FIG. 2 shows the schematic configuration of the first embodiment.

Next, a stationary portion of an arcuate second rotational element 12 (also defined as a rotation mechanism) is attached to a movable portion of the rotational element 11. At this time, the rotational element 11 and the rotational element 12 are configured such that, as shown in FIG. 2, the rotation axis 22 of the second rotational element 12 that represents the center of rotation of a movable portion of the second rotational element 12 is perpendicular to the rotation axis 21 of the first rotational element 11 that represents the center of rotation of the movable portion of the first rotational element 11.

A needle guide 13 is attached to the movable portion of the second rotational element 12.

The needle guide 13 has a cutout. By inserting a needle-like instrument 10 along the cutout, the insertion direction of the instrument 10 is guided.

The first rotational element 11 and the second rotational element 12 are optionally provided with scale-like position detection units 6a and 6b, with which the rotation angle of each rotational element can be detected.

Thus, in use, the medical support device is positioned on an object such as a human torso and the two rotational elements are rotated to define an optimal or predefined trajectory for a needle like element when inserted along the cut-out of the needle guide.

Detailed Description of Each Mechanism

The arrangement of degree of freedom of each rotational element of the mechanical portion 1 and the range of movement thereof will be described with reference to FIG. 2.

In FIG. 2, the needle guide 13 and the position detection units 6a and 6b are omitted for simplification. The needle-like instrument 10 is also omitted. Instead, a straight line 20 showing the direction of the instrument is depicted.

First, how coordinate axes are defined in this embodiment will be described. The XZ plane is defined as a plane containing the bottom surface of the mechanical portion, and the Y-axis is defined as an axis perpendicular to the XY plane. Hereinafter, a coordinate (x, y, z) shows the values of the X-axis, Y-axis, and Z-axis.

The movable portion of the first rotational element 11 is arranged such that the rotation axis 21 is perpendicular to the bottom surface. In FIG. 2, the movable portion of the first rotational element 11 is arranged such that the rotation axis 21 coincides with the Y-axis. In this embodiment, the movable portion of the first rotational element 11 is rotatable at least ±180 degrees.

Next, the movable portion of the second rotational element 12 is arranged such that the rotation axis 22 is perpendicular to the rotation axis 21 of the first rotational element 11. In FIG. 2, the movable portion of the second rotational element 12 is arranged such that the rotation axis 22 coincides with the Z-axis. However, the rotation axis 22 is not fixed. When the movable portion of the first rotational element 11 is rotated an arbitrary angle, the rotation axis 22 is also rotated. For example, when the first rotational element 11 is rotated 90 degrees, the rotation axis 22 coincides with the X-axis.

When 0 degrees is defined as a position corresponding to the Y-axis, the movable portion of the second rotational element 12 is rotatable in both positive and negative directions with respect thereto.

Figures 3A, 3B, 3C:
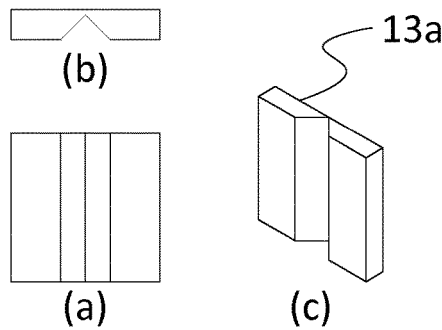
FIGS. 3A, 3B, and 3C show three views of a first example of a needle guide.
Figures 4A, 4B, 4C:
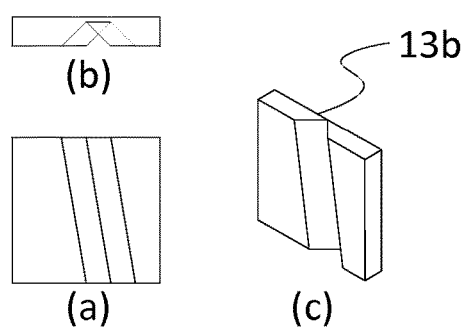
FIGS. 4A, 4B, and 4C show three views of a second example of a needle guide.

Needle guides 13 facing in different directions as shown in FIGS. 3A to 3C and FIGS. 4A to 4C are interchangeable with each other. Thus, several needle guides with the configuration of FIG. 3 and/or FIG. 4 may be positioned on the needle guide. FIG. 3A and FIG. 4A are front views, FIG. 3B and FIG. 4B are plan views, and FIG. 3C and FIG. 4C are isometric views. The needle guide 13b shown in FIGS. 4A to 4C is provided with a cutout so as to guide a needle-like instrument 10 in a direction that does not pass through the intersection 23 of the rotation axis 21 of the first rotational element 11 and the rotation axis 22 of the second rotational element 12.

On the other hand, the needle guide 13a shown in FIGS. 3A to 3C is provided with a cutout so as to guide a needle-like instrument 10 in a direction that passes through the intersection 23 of the two rotation axes.

In this embodiment, for simplification, a description will be given of a case where only the needle guide 13b shown in FIGS. 4A to 4C is used. Similarly in FIG. 4, the needle guides can be formed with a different angle for the cutout. This provides for needle guides that will guide a needle to an entry point having a different proximity to the intersection of the rotation axis of the two rotational elements.

In some embodiments, as shown in FIGS. 3 and 4, the cutout of the needle guide is triangular in shape. In other embodiments the cutout is a semicircle, square, rectangular, or having some other shaped. In other embodiments, instead of a cutout as described herein, the needle guide 13 may contain a through-hole that can be used to guide the needle. In some embodiments, in addition to a cutout, an additional element may be incorporated as part of the needle guide. This additional element may be configured to hold and then release the needle after positioning, to, for example, allow a patient to resume breathing after needle placement.

Operation

Figure 8A:
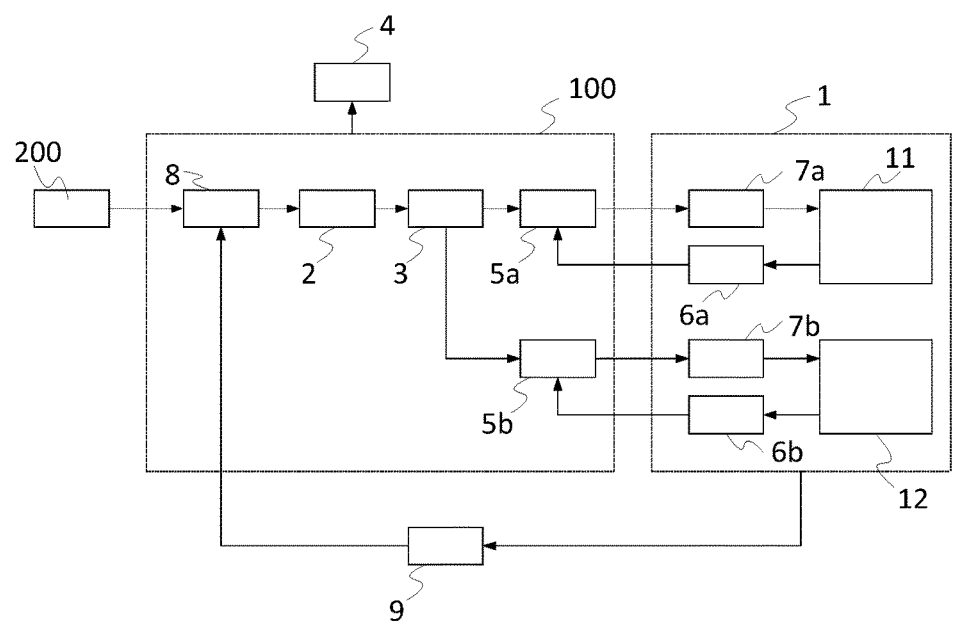
FIG. 8A is a block diagram of the second embodiment.
Figure 8B:
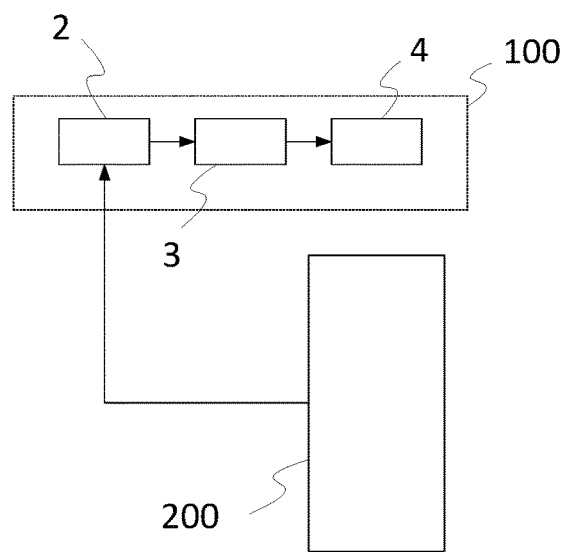
FIG. 8B is a block diagram of the first embodiment.

FIG. 8B is a block diagram showing a system configuration, including a user, in this embodiment. The operation of each block and input and output signals in this embodiment will be described with reference to FIG. 8B.

The user specifies a plurality of target positions in the coordinate system of the medical support device via an input device 200.

An angle calculation unit 2 finds two combinations of target angles of the two rotational elements for each of the input target positions, and outputs them to an interference analysis unit 3. For example, when two target positions Pa (xa, ya, za) and Pb (xb, yb, zb) are input, combinations of target angles ($\theta a1$, $\theta a2$) and ($\theta a1'$, $\theta a2'$) for the target position Pa are output. Combinations of target angles ($\theta b1$, $\theta b2$) and ($\theta b1'$, $\theta b2'$) for the target position Pb are output.

In some embodiments, the target positions are input as coordinates. In other embodiments, the target positions are provided by the user by indicating the position directly on a tomographic medical image (e.g., via a touch or a pointing device).

The calculation may be a calculation of general inverse kinematics, so the description thereof will be omitted.

The interference analysis unit 3 finds the equations of straight lines 20 showing the directions in which needle-like instruments 10 are inserted, from the combinations of target angles input from the angle calculation unit 2. Then, the interference analysis unit 3 finds the distances between straight lines to different targets from the found equations of straight lines.

For example, the interference analysis unit 3 finds the equations of straight line La and straight line La' from the combinations of target angles ($\theta a1$, $\theta a2$) and ($\theta a1'$, $\theta a2'$), and finds the equations of straight line Lb and straight line Lb' from the combinations of target angles ($\theta b1$, $\theta b2$) and ($\theta b1'$, $\theta b2'$).

Then, the interference analysis unit 3 selects the combination that is largest in distance between straight lines from four combinations La-Lb, La-Lb', La'-Lb, and La'-Lb'. In this embodiment, La-Lb is selected. The selected combination of target angles is presented on a presentation portion 4.

Presentation portion 4 may be, for example, a display unit such as a monitor, and it may be integrated into the display of the medial image. Alternatively, the presentation portion may be, for example, a small display located on the device.

At this time, the calculation performed in the interference analysis unit 3 is a general calculation for finding the distance between two straight lines in a three-dimensional space, so the detailed description thereof will be omitted.

The user optionally confirms the target angles presented on the presentation portion 4, and rotates the first rotational element 11 in FIG. 1 and the second rotational element 12 in FIG. 1 manually such that they are at the presented target angles. At this time, the user changes the position of the first rotational element 11 and the second rotational element 12 manually by referring the position detection units 6a and 6b provided on the rotational elements 11 and 12. In alternative embodiments, the positioning of rotational elements 11 and 12 is automated and the presentation portion is optional.

As a result, the needle guide 13 faces the target position Pa. By inserting a needle-like instrument 10a along the cutout of the needle guide 13 in this attitude, the instrument can be inserted at the target position Pa as shown in FIG. 5A.

Next, in order to puncture the target position Pb, with the instrument boa remaining inserted, as with the target position Pa, the movable portions of the rotational elements are moved such that the rotational elements 11 and 12 are at the target angles $\theta b1$ and $\theta b2$ thereof.

As a result, the needle guide 13 faces the target position Pb. By inserting a needle-like instrument 10b along the cutout of the needle guide 13 in this attitude, the instrument can be inserted at the target position Pb.

Figures 5A, 5B:
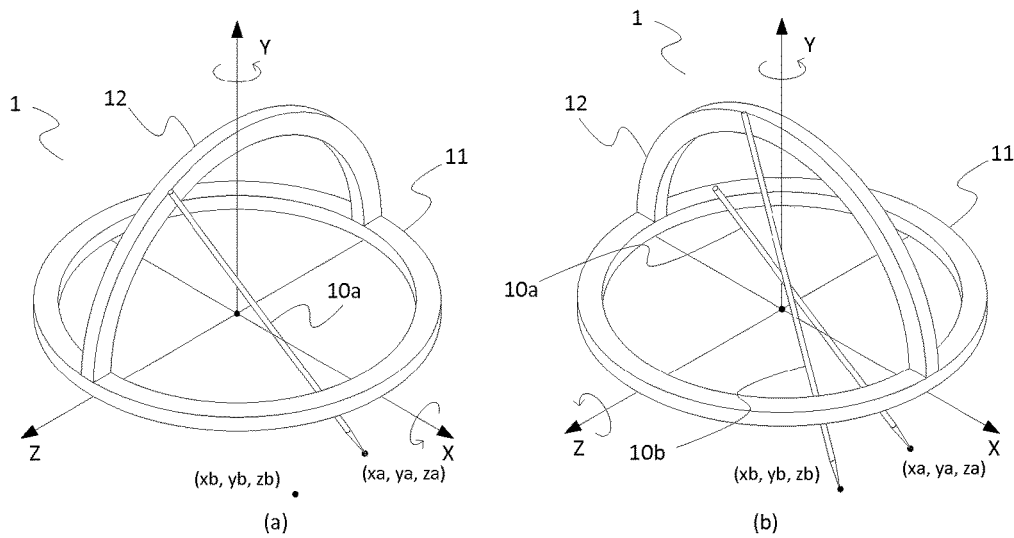
FIGS. 5A and 5B show the state of needles during puncture.

Thus, as shown in FIG. 5B, needle-like instruments 10 are inserted at both the target position Pa and the target position Pb.

Figure 9:
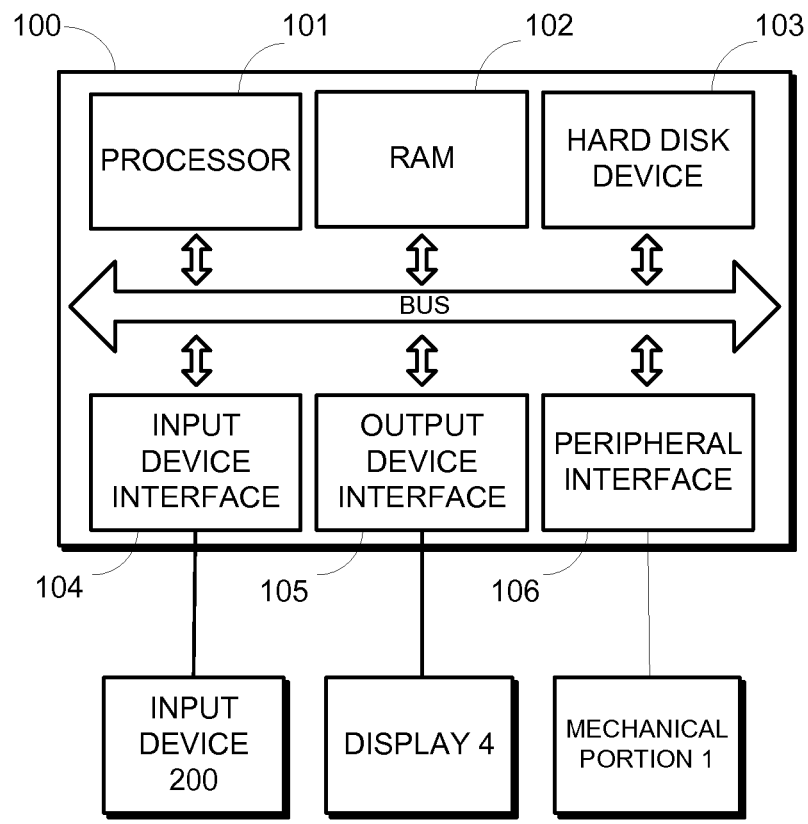
FIG. 9 is a block diagram of a computer system as described here.

FIG. 9 illustrates an example of hardware of the computing unit 100. A processor 101 reads and executes a program code stored in a hard disk device 103 to execute a various type of process and control. A ram 102 temporarily stores information pieces, such as a program code executed by the processor 101. The hard disk device 103 stores a program code and a various type of date for performing processes and/or operations described with FIG. 8B above. An input device interface 104 receives a user input to the computer unit 100 from an input device 200 such as a keyboard, a mouse, a joystick, or a touch pad. An output device interface 105 outputs data to an output device such as a display and a recording apparatus. A peripheral interface 106 performs data and/or signal communication with an external device (for example, the Mechanical portion 1).

In this way, in a medical support device that supports puncture having two rotational elements, when inserting instruments at a plurality of different target positions, the instruments can be inserted at their target positions without interfering with each other.

In this way, in a medical support device that supports puncture having two rotational elements, when inserting instruments at a plurality of different target positions, the instruments can be inserted at their target positions without interfering with each other.

The mechanical portion 1 may be fixed to the object with tape, adhesive, or the like. The base 15 may be provided with a part to which a belt-like instrument is attached, and the mechanical portion 1 may be fixed to the object with a belt or the like. If the mechanical portion 1 can be fixed to the object with bolts, the base 15 may be provided with holes into which bolts or other fixation elements are inserted.

The rotational elements do not necessarily have to be annular (ring-shaped) and arcuate, and only have to be mechanisms having two orthogonal rotation axes.

The position detection units 6 do not necessarily have to be scale-like, and may be optical or electrical detectors, for example, encoders or potentiometers. In that case, the present angle can be displayed on the presentation unit 4 or the like.

In these embodiments, the movable portion of the first rotational element 11 can rotate ±180 degrees. However, the present invention is not limited to this. The present invention can be applied even if the rotation angle is less than ±180 degrees, such as ±145 degrees, ±90 degrees, or ±45 degrees.

The range of movement of the movable portion of the second rotational element 12 can be wide. The wider the range of movement, the wider the range of puncture from the same installation position. However, in the present invention, this range is not limited as long as puncture target positions are within the range.

The shape of the needle guide 13 does not necessarily have to be a cutout such as the triangular-shaped cutout as shown in FIGS. 3 and 4, and may be, for example, a tubular shape, a cylindrical shape, a trough shape, or such a shape that two parts hold an instrument there between (for example, two triangular, rectangular, or semicircular cutouts in two parts of a needle guide that are held or hinged together).

In some embodiments, for simplification, a description has been given of a case where only the needle guide 13b is used. However, locations in the vicinity of the origin cannot be punctured with only the needle guide 13b. In such a case, by interchanging the needle guide 13b with the needle guide 13a, the puncture of the vicinity of the origin is made possible.

Although, in this embodiment, two types of needle guides 13 are shown, the present invention is not limited to this, and three, four, five or more needle guides 13 of different angles may be used. In some embodiments, the needle guide 13 is inclined in a plane in which the second rotational element 12 rotates. However, as long as the straight line showing the guiding direction does not pass through the intersection 23 of the rotation axes of the two rotational elements, the present invention is not limited to this, and the needle guide 13 may be inclined in another direction, or may be translated.

The needle guide 13 may have a mechanism having a degree of freedom such as those shown in FIGS. 10A to 10C, FIGS. 11A to 11C, and FIGS. 12A to 12C so that the direction and angle of puncture can be changed freely.

Figures 10A, 10B, 10C:
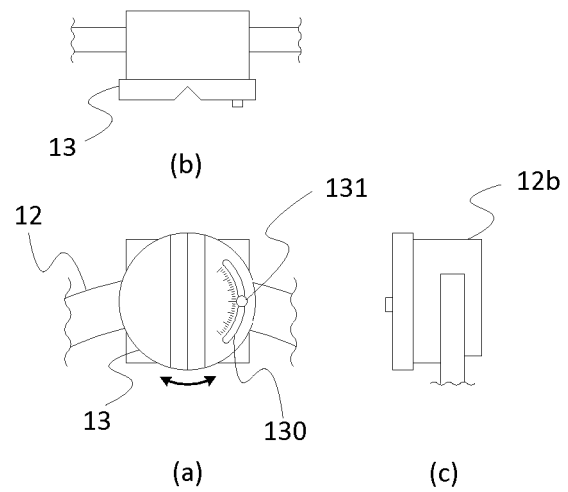
FIGS. 10A, 10B, and 10C show a first needle guide mechanism having a degree of freedom.
Figures 11A, 11B, 11C:
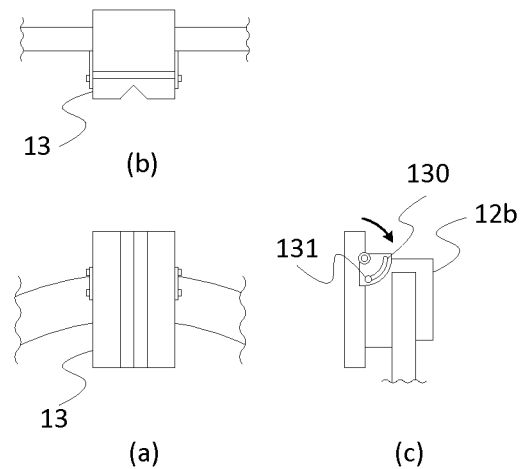
FIGS. 11A, 11B, and 11C show three views of a second needle guide mechanism having a degree of freedom.
Figures 12A, 12B, 12C:
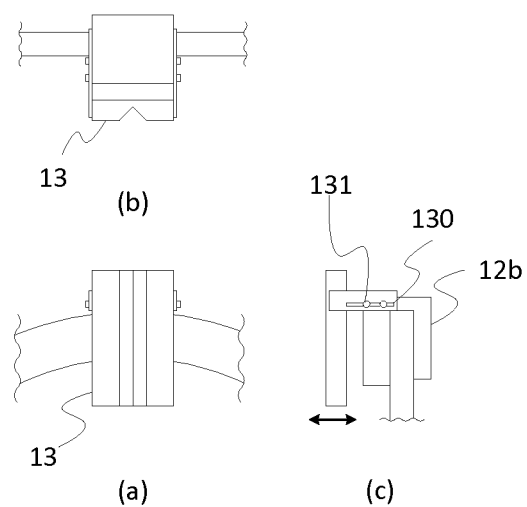
FIGS. 12A, 12B, and 12C show three views of a third needle guide mechanism having a degree of freedom.

FIGS. 10A, 11A, and 12A are front views, FIGS. 10B, 11B, and 12B are plan views, and FIGS. 10C, 11C, and 12C are side views. The needle guide 13 is attached to the movable portion 12b of the second rotational element 12, and is movable with only a predetermined degree of freedom owing to a groove 130 provided in the direction of degree of freedom and a fixing screw 131. By tightening the fixing screw 131, the needle guide 13 can be fixed at a set angle.

FIG. 10 shows an example of a configuration that achieves a degree of freedom about a rotation axis parallel to the rotation axis of the second rotational element. FIG. 11 shows an example of a configuration that achieves a degree of freedom about a rotation axis perpendicular to the rotation axis of the second rotational element. FIG. 12 shows an example of a configuration that makes it possible to translate the needle guide 13 in the direction of the rotation axis of the second rotational element without changing the puncturing direction.

Although the mechanisms of the needle guide 13 shown in FIGS. 10A to 10C, FIGS. 11A to 11C, and FIGS. 12A to 12C are described independently of one another, they may be combined, or a mechanism having another configuration may be provided in order to achieve the same degree of freedom.

In some embodiments, only one combination determined by the interference analysis unit 3 is presented on the presentation portion 4. However, the present invention is not limited to this. For example, four combinations of straight lines and the distance between two straight lines in each combination may be presented so that the user can select which combination to use. Combinations causing interference are preferably avoided.

The number of puncture target positions is two. However, the present invention is not limited to this. The number of puncture target positions may be three, four, five, or more. In that case, the number of combinations processed in the interference analysis unit 3 is 2 to the power of n, where n is the number of targets.

With more target positions, the possibility that interference between instruments occurs is increased. Therefore, one or more of the needle guide 13 can be configured to direct a needle to a point further away from the origin, or a plurality of needle guides 13 can be configured to face in different directions so that they can be interchanged.

Second Embodiment

Configuration

A second embodiment of the present invention will be described with reference to FIG. 6 to FIG. 8A. First, the schematic configuration of a mechanical portion of a medical support device of this embodiment will be described with reference to FIG. 6 and FIG. 7.

Mechanical Configuration

Figure 6:
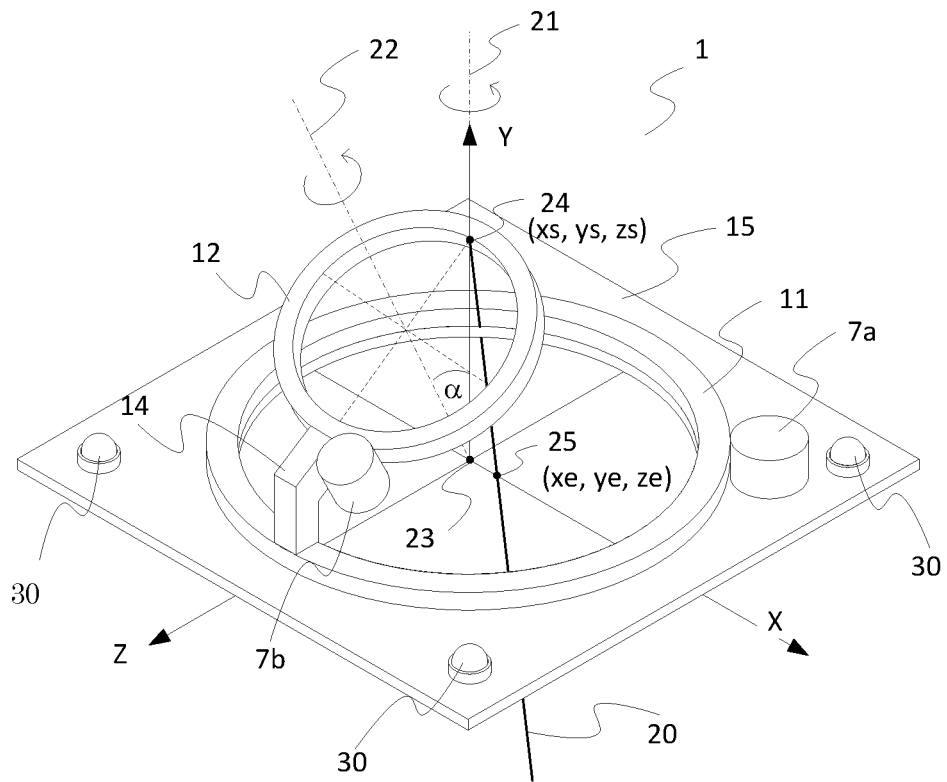
FIG. 6 shows the schematic configuration of a mechanical portion of a second embodiment.

In FIG. 6, the structure of a movable portion in each rotational element is omitted for simplification. The embodiments of the rotational elements as described in U.S. Pat. Pub. 2014/027979 are herein incorporated by reference. In use, a base 15 of a mechanical portion 1 is first fixed and installed on an object to be punctured with a fixing unit (not shown). This includes, for example, the torso of a patient.

Figure 7:
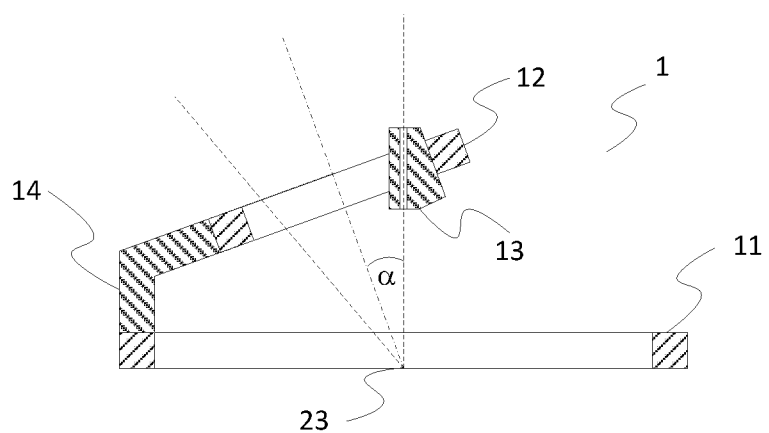
FIG. 7 is a schematic sectional view of the mechanical portion of the second embodiment.

FIG. 7 is a sectional view of the configuration of FIG. 6 cut along the ZY-plane.

A stationary portion of an annular, or ring shaped first rotational element 11 is attached to the fixing unit.

A stationary portion of an annular second rotational element 12 is attached to a movable portion of the rotational element 11 with a supporting portion 14 there between. The rotational element 11 and the rotational element 12 are configured such that the rotation axis 22 of the movable portion of the second rotational element 12 is inclined at a predetermined angle α with respect to the rotation axis 21 of the movable portion of the first rotational element 11 and intersects therewith at the origin of the XYZ coordinate.

A needle guide 13 (not shown) is attached to the movable portion of the second rotational element 12. As in the first embodiment, the needle guide 13 has a cutout. By inserting a needle-like instrument 10 along the cutout, the insertion direction of the instrument 10 is guided. The straight line 20 shows the direction in which the needle guide 13 guides a needle-like instrument 10 in this embodiment.

As shown in the block diagram of FIG. 8B, the first rotational element 11 and the second rotational element 12 are provided with position detection units 6a and 6b, with which the rotation angle of each rotational element can be detected. The position detection units 6a and 6b output the signal indicating the rotation angle of each rotational elements 11 and 12. The signals output from the position detection units 6a and 6b are input to the control portions 5a and 5b.

The first rotational element 11 is connected to a drive source 7a provided on the base by a transmission mechanism (not shown), and the movable portion is driven by the drive source 7a. Similarly, the second rotational element 12 is connected to a drive source 7b provided on the supporting portion 14 by a transmission mechanism (not shown), and the movable portion is driven by the drive source 7b.

In some embodiments, markers 30 are attached to the medical support device. Thus, some embodiments include at least three markers 30 that can be imaged by MRI, CT, or both MRI and CT are attached to the mechanical portion 1. In some embodiments, four, five, or more markers 30 are attached.

System Configuration and Operation

Next, a system in this embodiment will be described with reference to the block diagram of FIG. 9. Here, the hard disc device 103 in FIG. 9 stores a program code and a various type of date for performing processes and/or operations described with FIG. 8A below.

First, a tomographic image of the mechanical portion 1 installed on the object is obtained by MRI or CT. A coordinate conversion unit 8 detects the plurality of markers 30 that are attached to or otherwise installed on the mechanical portion 1 from the tomographic image, and calculates the installation position and attitude of the mechanical portion 1 based on the medical image from the positional relationship between the plurality of markers 30. The user specifies a plurality of target positions on the tomographic image. These positions are sent to computing unit 100 which includes a coordinate conversion unit 8, angle calculation unit 2, interference analysis unit 3, and one or more control portions 5a and 5b.

The coordinate conversion unit 8 converts the plurality of target positions specified on the tomographic image into a plurality of target positions in the coordinate system of the mechanical portion 1 on the basis of the calculated installation position and attitude of the mechanical portion 1, and outputs them to an angle calculation unit 2.

An angle calculation unit 2 finds two combinations of target angles of the two rotational elements for each of the input target positions, and outputs them to an interference analysis unit 3. For example, when two target positions Pa (xa, ya, za) and Pb (xb, yb, zb) are input, combinations of target angles (θa1, θa2) and (θa1', θa2') for the target position Pa are output. Combinations of target angles (θb1, θb2) and (θb1', θb2') for the target position Pb are output.

The interference analysis unit 3 finds the equations of straight lines 20 showing the directions in which needle-like instruments 10 are inserted, from the combinations of target angles input from the angle calculation unit 2. Then, the interference analysis unit 3 finds the distances between straight lines to different targets from the found equations of straight lines.

For example, the interference analysis unit 3 finds the equations of straight line La and straight line La' from the combinations of target angles (θa1, θa2) and (θa1', θa2'), and finds the equations of straight line Lb and straight line Lb' from the combinations of target angles (θb1, θb2) and (θb1', θb2').

Then, the interference analysis unit 3 selects the combination that is largest in distance between straight lines from four combinations La-Lb, La-Lb', La'-Lb, and La'-Lb'. In this embodiment, La-Lb is selected as the combination that is largest in distance between straight lines. The largest distance is selected to minimize the possible interference. In other embodiments, it is unnecessary to select the combination that is largest in distance.

In this embodiment, the interference analysis unit 3 outputs target angle θa1 to a control portion 5a that is a control portion of the first rotational element 11. In addition, the interference analysis unit 3 outputs target angle θb1 to a control portion 5b that is a control portion of the second rotational element 12.

The control portion 5a controls the position of the movable portion of the first rotational element 11 by outputting a drive command to the drive source 7a provided to the first rotational element 11 on the basis of target angle θa1 input from the interference analysis unit 3, and the position detection unit 6a attached to the first rotational element 11. Specifically, the control portion 5a outputs a drive command based on the difference between the present angle obtained from the position detection unit 6a and target angles θa1, and performs control such that target angle θa1 is reached.

Similarly, the control portion 5b controls the position of the movable portion of the second rotational element 12 by outputting a drive command to the drive source 7b provided to the second rotational element 12 on the basis of target angle θb1 and the signal obtained from the position detection unit 6b attached to the second rotational element 12.

Alternatively, instead of outputting a drive command to the control portions of the rotational elements, the interference analysis unit 3 may output the rotational position of the rotational elements and then allow for manual adjustment of the rotational elements. In another alternative, the interference analysis unit 3 may output both the drive command to cause the rotation of the rotational elements and also the rotational positions so that the automated rotation may be verified by the user.

As a result, the needle guide 13 faces the target position Pa. By inserting a needle-like instrument 10a along the cutout of the needle guide 13 in this attitude, the instrument can be inserted at the target position Pa.

Next, in order to puncture the target position Pb, with the instrument boa remaining inserted, the drive sources 7a and 7b are driven such that the rotational elements 11 and 12 are at the target angles θb1 and θb2 thereof. As a result, the needle guide 13 faces the target position Pb. By inserting a needle-like instrument 10b along the cutout of the needle guide 13 in this attitude, the instrument 10b can be inserted at the target position Pb without interfering with the instrument boa.

Third Embodiment

The third embodiment of the present invention will be described with references to FIG. 13 to FIG. 14. First, the apparatus of using interchangeable needle guides of different designs will be described with reference to FIG. 13. However, the needle guides as described in the first and second embodiments may also be combined with the teachings of this embodiment.

Figure 13:
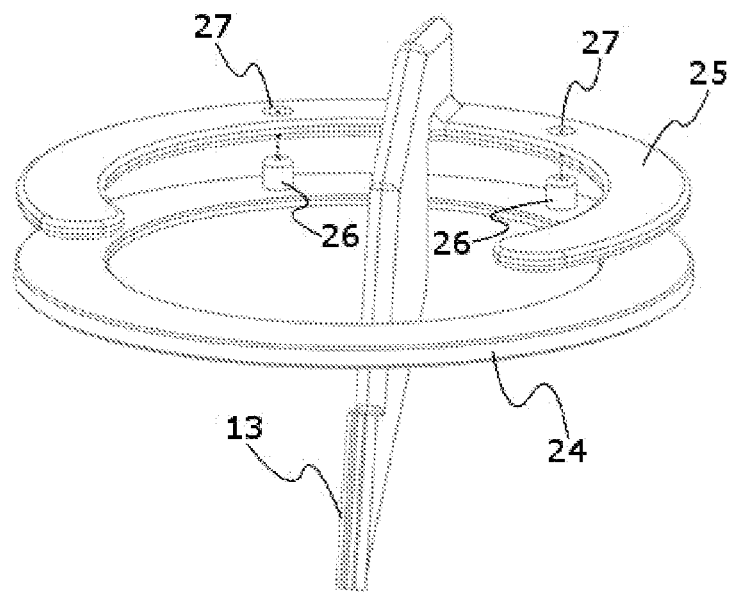
FIG. 13 shows the schematic configuration of a mechanical portion of a third embodiment.
Figure 14:
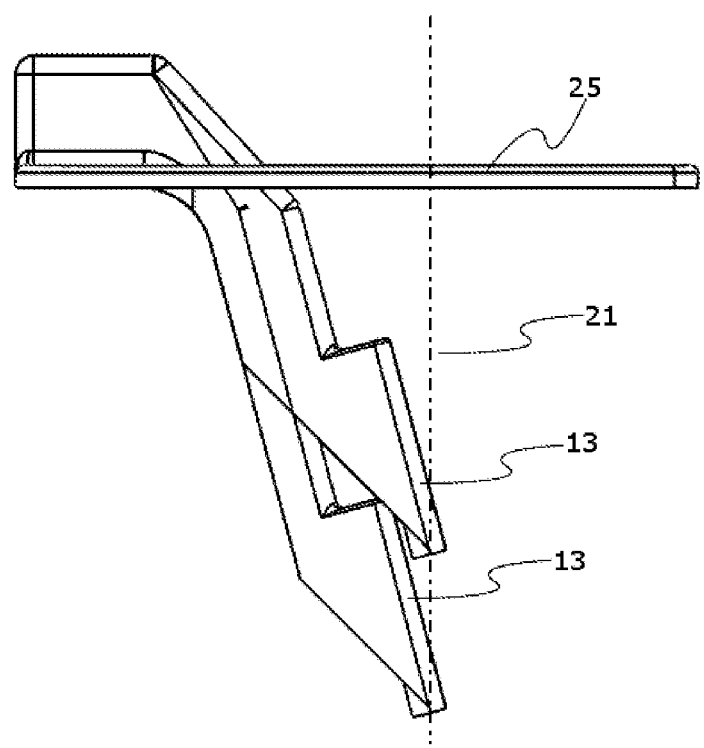
FIG. 14 shows a cut away view of the schematic configuration of a mechanical portion of a third embodiment.

In FIG. 13, an example of apparatus of a detachable needle guide is presented. For simplicity, only the two mating surfaces 24 and 25 are shown. When combined, these surfaces form a second rotational element 12 as described, for example, in FIG. 6. The lower mating surface 24 is attached to the first rotational element or base (not shown).

The needle guide can be attached and detached at the will of the user. For example, the needle guide can be slid into and out of a groove, onto a pin-like structure, or it can contain a snap closure for securing and removing from the apparatus. The removable mating surface 25 of the rotational element 12 includes a needle guide 13. The removable mating surface of the needle guide 25 can be attached and removed from a secure position by pressing bosses 26 on the top of the lower mating surface 24 into holes 27 on the upper mating surface of the needle guide 25.

Each needle guide 13 can have a unique shape such that a needle-like instrument 10 can be inserted without colliding with previously inserted needles.

In one exemplary embodiment, the cutouts on each needle guide can be formed so they rest at different heights. This will guide the needle to an entry point which would be above or below the intersection of the rotation axis of the two rotational elements 11 and 12. In FIG. 14, two needle guides 13 and 13b of different heights are overlaid. In this figure, the example shows the different points the guide 13 meets with the rotational axis of the lower ring 21.

Fourth Embodiment

Figures 15A, 15B, 15C:
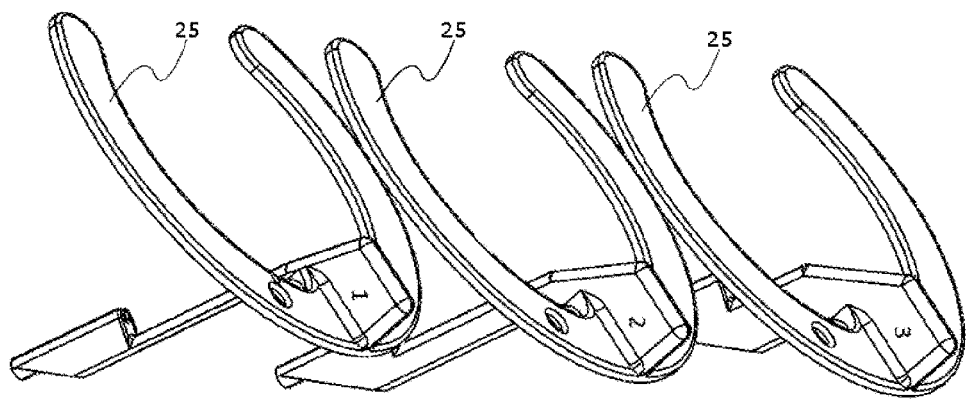
FIG. 15A-15C each shows schematic configurations of a mechanical portion of a fourth embodiment.

A fourth embodiment of the present invention, a system of using a unique and preselected needle guide for each individual needle inserted, will be described with reference to FIGS. 15A-15C.

During insertion of multiple needles, each needle guide can be used in a predetermined order. These needle guides can vary in design to ensure each needle has a unique insertion path and will not interfere with previously inserted or future needles.

The user can determine which needle guide to use by markings on the needle guide that are unique to each design.

The markings can be include numbers, letters, colors, or names, or any variation or combination there-of. FIG. 15 shows an example of three differently designed needles guides each having a unique marking on them for identification.

The procedural workflow or software can tell the user which sequence to use.

The software can modify the kinematics algorithm to adjust for the unique design of each needle guide.

The user 19 will select the first needle guide 13, as denoted by the workflow, and attach it to the second rotational element 12. The user 19 will sent the target to the controller through the software and the robot will rotate the rotational elements to align the first needle guide to the target. The user 19 will then insert the needle through the guide until it reaches the target. After the needle reaches the target, the user 19 will remove the first needle guide 13 from the second rotational element 12 and discard of it. The user 19 will then take the second needle guide 13, as denoted by the workflow, and attach it to the second rotational element 12. The user 19 will send the target to the controller through the software and the robot will rotate the rotational elements to align the second needle guide to the target. The user will not have to change any settings of the software since the software already knows the order the needle guides will be used in. The user will insert the needle and repeat this process until all needles are placed.

Fifth Embodiment

A fifth embodiment of the present invention will be described with references to FIG. 16 to FIG. 17.

First, the system of using a user-selected needle guide for each individual needle inserted will be described.

During insertion of multiple needles, the user can decide which needle guide to use so the insertion of the next needle will not collide with previously inserted needles. Alternatively, the needle guides can be provided in a kit with a predetermined order, where each of the needle guides is provided such that when used in order, the inserted needles will not collide with each other, even without the need to move the patient's skin or prior needle.

The device and associated software can detect which needle guide is inserted and update the kinematics algorithm to match the current guide.

Next, the system of sensing which needle guide design for each needle inserted will be described with reference to FIG. 16 to FIG. 17.

Figure 16:
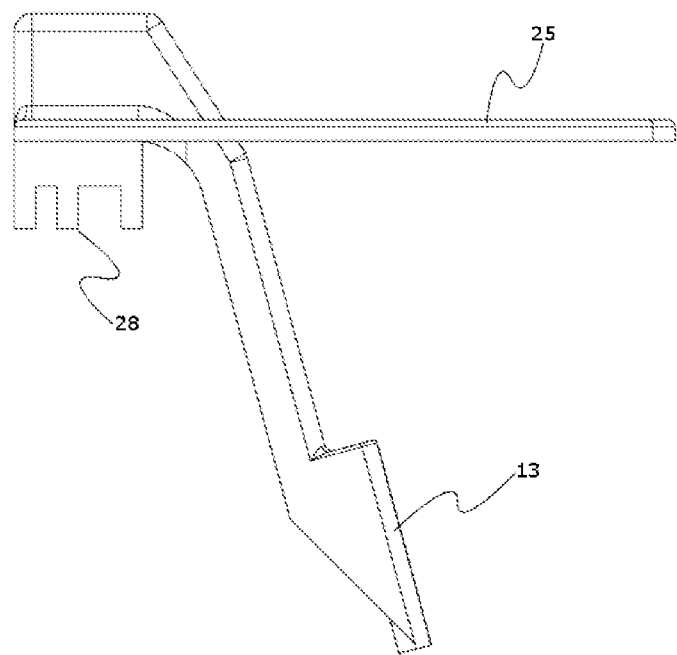
FIG. 16 shows a cut away view of the schematic configuration of a mechanical portion of a fifth embodiment.

In FIG. 16, an example of a needle guide used in a system where the needle guide identity is sensed using a key design 28 is shown. For simplicity, only the needle guide and key 28 is shown. In this design, different pins are depressed depending on the shape of the key 28 attached to the needle guide. Based upon the combination of which pins are pressed, the identity of the needle guide can be deciphered.

Figure 17:
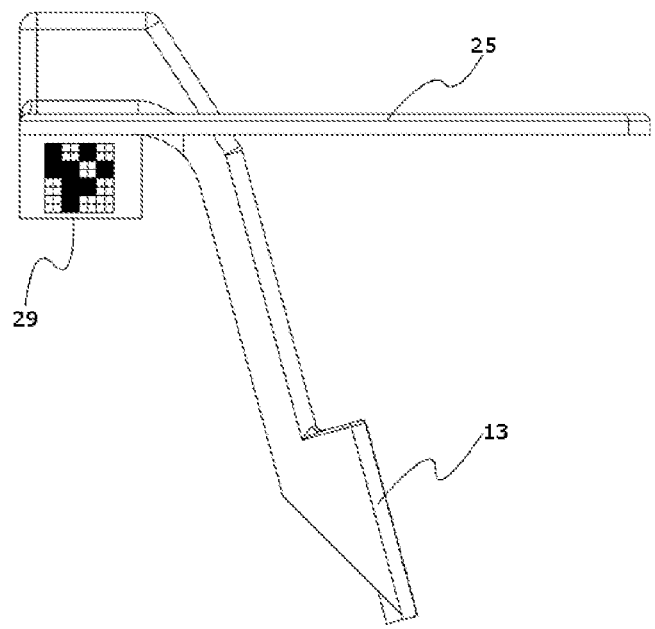
FIG. 17 shows a cut away view of the schematic configuration of a mechanical portion of a fifth embodiment.

In FIG. 17, an example is shown of a system where an optical sensor 29 detects a unique marking on the needle guide to identify which is being used. For simplicity, only the marking is shown. In this design, the visual markings are detected by an optical sensor 29 and the software can determine which needle guide design matches the detected markings.

In other embodiments, other ways of determining which needle guide is provided in the medical support device may be used. These methods may include other types of sensors, pins, or other structures that allow information to be provided to the kinematics algorithm so the insertion of the needle with the specific holders can be defined.

Sixth Embodiment

Figure 18A:
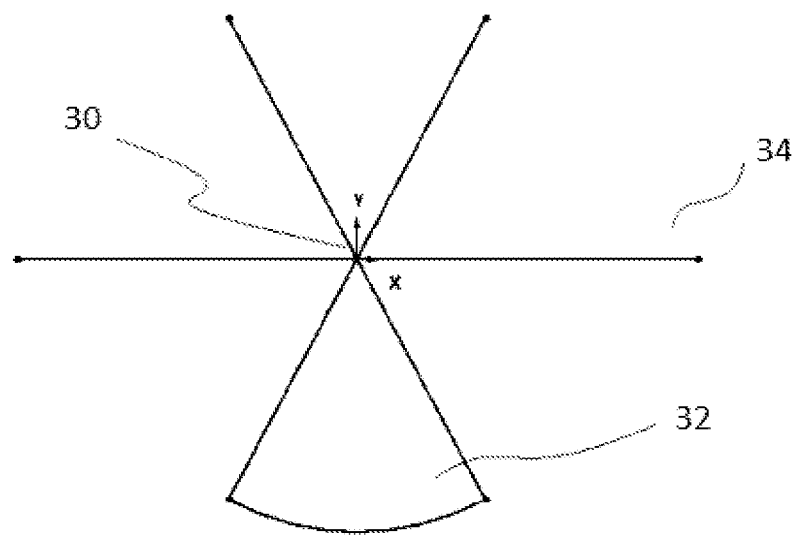
FIG. 18A is a schematic showing the cone-shaped volume a needle-like instrument can pass through during rotation of the medical support device.

As shown in FIG. 18, a pivot point 30 exists where, when using a needle guide 13, a needle or other needle like instrument must pass through in order to reach all target positions within a reachable volume 32. The needle reachable volume 32 is a cone shaped volume where the tip of the cone is located at the pivot point 30 and extends into the patient. The pivot point 30 can be located in a number of locations relative to the skin 34 of the patient. For example the pivot point 30 can be above the skin 34, on the skin 34, or within the patient. This can be defined by the design of the medical support device and optionally any other device or component mounted on the patient. For example, the addition of an RF coil beneath the medical support device where the device initially has a pivot point at the skin moves the pivot point to a position above the skin's surface. If the pivot point 30 coincides with a location on the skin 340f the patient (as shown in FIG. 18) or within a patient then this prevents accurate targeting when using multiple needles with a needle guide 13. For insertion, each needle path must be altered to move around prior needles because prior needles will pass through the pivot point 30. The pivot point 30 can also be offset from intersection 23. In the case where the pivot point 30 is located above the patient a desired needle path for multiple needles through the pivot point can be maintained even when using multiple needles without the needles overlapping. For example after the first needle is placed, user 19 can tilt the first needle to move the needle out of the way while inserting the next needle. Due to the first needle already being located within the patient, the tip will be stationary and just the portion of the needle remaining outside the patient will bend away from pivot point 30.

Height Change Discussion

Figure 18B:
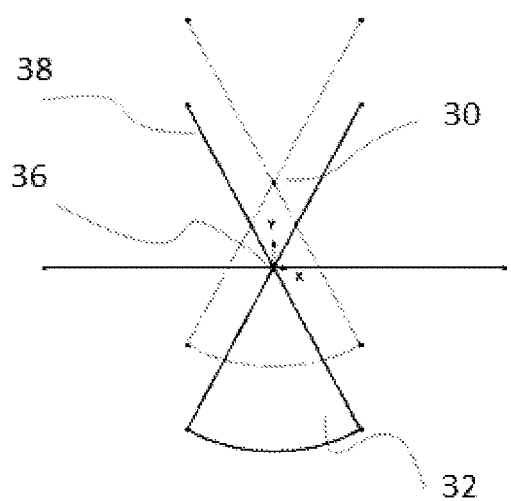
FIG. 18B is a schematic showing cone-shaped volume for two needle-like instruments where the height of the needle guides are different.
Figure 18C:
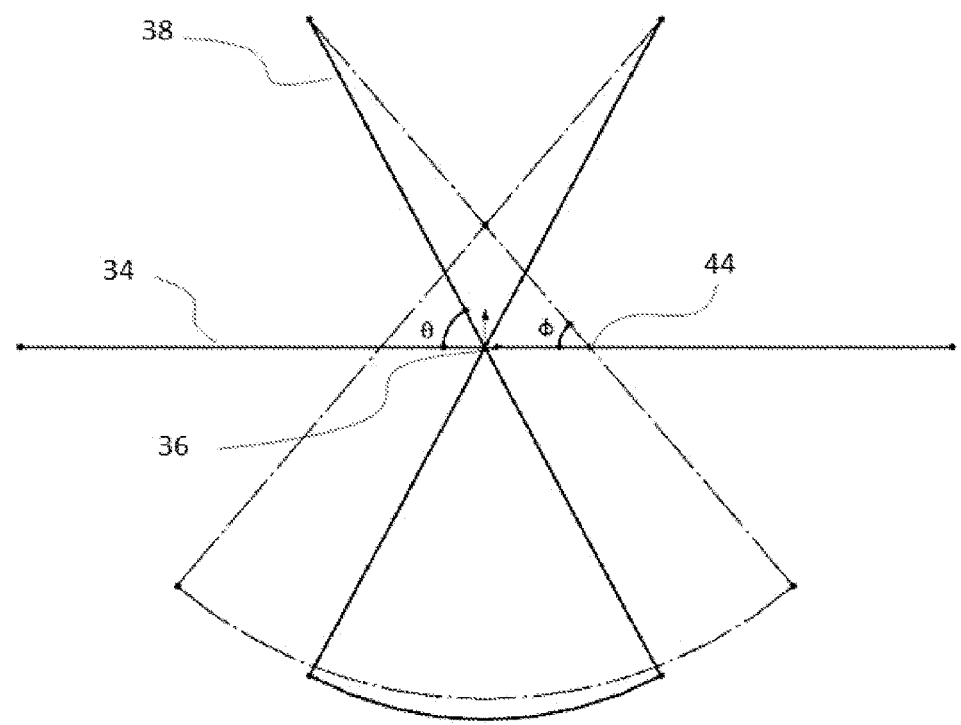
FIG. 18C is schematic showing cone-shaped volumes for two needle-like instruments where the angle of the needle guides are different.

In the next embodiment, as indicated in FIG. 18B, the medical support device has a remote center of motion (RCM) which is located above the subject when placed on the subject. The height of the needle guide is changed, thus modifying the pivot point 30 of the needle. As shown in FIG. 18B, if the same angle is maintained and the height is shifted up in the Y direction then the pivot point 30 will shift upwards. This shift has multiple effects. One effect is the shift in initial puncture point 36 due to shift of initial needle path 38. A new puncture point 40 is created following needle path 42. For example if the pivot point 30 is originally at the surface of the skin, and then the pivot point 30 is shifted upward then the initial puncture point 36 will be shifted outward. Another effect is the change in reachable volume 32 if we assume a fixed needle length. By changing the pivot point the reachable volume 32 is shifted. Thus, in use, a first needle-like instrument is inserted at a first puncture starting point and then the medical support device (or a portion of the medical support device) is moved upwards, away from the patient's skin. Next, a second needle-like instrument is inserted into a second puncture starting point that is different from the first puncture starting point.

Angle Change Discussion

In the embodiments where the angle of the needle guide is changed, there are multiple effects. These effects are similar to the effects when changing the height of the needle guide as described in the previous embodiment. If the height is maintained, the shift in angle will create new puncture points. For example in FIG. 18C, θ represents the original angle of initial needle path 38 with respect to the surface of the skin 34 when the needle enters the skin at the first puncture starting point 36 and Φ represent the angle between a second needle path 42 and skin 34 created by modifying the needle guide angle. With the modified angle, instead of entering the patient at the initial puncture starting point 36, the entry point is shifted outward to a second puncture starting point 44. Another effect can be seen when the needle lengths are maintained. The shape of the cone that represents the reachable volume 32 of the needle is modified. In the case with angle θ the cone is narrower and can reach deeper past the surface. In the case with angle Φ the cone is wider and reaches a volume that is shallower. Thus, in use, a first needle-like instrument is inserted at a first puncture starting point where the needle guide holds the needle at an angle θ. A second needle-like instrument is inserted via a second needle guide that holds the needle at angle Φ. This second needle is inserted into a second puncture starting point that is different from the first puncture starting point.

Combination of angle change and height change of needle guide

It is apparent that a combination of changing the height and angle of needle guide 13 will result in the combined effects of each individual change. For example the pivot point 30 can be maintained while changing the shape of the reachable volume of the needle by combining the effects of modifying the needle guide height and angle.

Example: Calculations

In the configuration of this example, the inclination a of the second rotational element is set to 20 degrees, and the diameter of the needle-like instruments 10 is set to 2 mm. The initial position of the first rotational element 11 is set to such a position that the second rotation axis 22 is in the YZ plane. The initial position of the second rotational element 12 is set to such a position that, when a needle guide 13 (different from the needle guide in this description) intersecting with the intersection 23 of rotation axes is attached, a straight line showing the guiding direction coincides with the Y-axis. The straight line showing the guiding direction of the needle guide 13 is set to be a straight line passing through two points (0 mm, 50 mm, 0 mm) and (5 mm, 0 mm, 0 mm) on the XYZ coordinate in a state where the mechanical portion 1 is at the initial position. This straight line is expressed by the following equation (1) using parameter t:

$$\begin{cases} x = 5t \\ y = 50 + -50t \\ z = 0 \end{cases} \quad (1)$$

Two target positions Pa (xa, ya, za) and Pb (xb, yb, zb) are set to Pa (10 mm, −50 mm, 20 mm) and Pb (−5 mm, −40 mm, 10 mm).

When target position Pa is input into the angle calculation unit 2, the following combinations of target angles of the two rotational elements are output:
(θa1=−91.11 degrees, θa2=40.23 degrees)
(θa1'=144.24 degrees, θa2'=−99.09 degrees)

Similarly, when target position Pb is input into the angle calculation unit 2, the following combinations of target angles of the two rotational elements are output:
(θb1=−124.11 degrees, θb2=8.87 degrees)
(θb1'=70.98 degrees, θb2'=−75.17 degrees)

Next, the interference analysis unit 3 finds straight lines La, La', Lb, and Lb' showing the guiding direction of the needle guide 13 in each attitude from the configuration of the mechanical portion 1 and the input combinations of target angles of the rotational elements.

Then, the interference analysis unit 3 finds the distance between two straight lines in each of four possible combinations La-Lb, La-Lb', La'-Lb, and La'-Lb'. In this example, the distance between two straight lines in each combination is as follows:

La-Lb: 3.65 mm
La-Lb': 4.45 mm
La'-Lb: 8.93 mm
La'-Lb': 2.28 mm

In this embodiment, the combination that is largest in distance between two straight lines is selected. Therefore, La'-Lb is selected. On the basis of this, the drive sources 7a and 7b drive the rotational elements toward the target angles.

Since the diameter of instruments 10 is set to 2 mm, even if this diameter is taken into account, two needle-like instruments 10a and 10b are 6.93 mm away from each other even when they are closest to each other, and therefore they can puncture their respective target positions without interfering with each other.

In this embodiment, the angle calculation unit 2, the interference analysis unit 3, and the control portion 5 are described as separate units. However, this is a conceptual separation. For example, these units may be incorporated in a CPU as pieces of software at the same time. Alternatively, a single software program may perform multiple functions. In some embodiments, one or more of the angle calculation unit 2, the interference analysis unit 3, and the control portion 5 is a dedicated piece of firmware.

In the embodiment described above, the number of puncture target positions is two. However, the present invention is not limited to this. The number of puncture target positions may be three, four, five or more. As more needles are used, the possibility that interference between the various instruments occurs is increased. Therefore, the needle guide 13 can be caused to face a point further away from the origin, or a plurality of needle guides 13 facing in different directions can be prepared. Thus, it is contemplated that a needle holder having needle guides 13 with only a small deflection from the intersection of the rotation axis of the two rotational elements may be used when only a few needles need to be place and needle guides having a greater deflection are used when more needles are indicated in a procedure. The needle placement apparatus can include interchangeable needles guides so the different to account for differences needed in the deflection.

Although a plurality of needle guides 13 facing in a plurality of directions are interchanged, the present invention is not limited to this. For example, needle guides facing in different directions may be provided at the positions of 0 degrees and 180 degrees of the movable portion of the second rotational element, and which needle guide to use may be selected on the basis of the analysis result of the interference analysis unit 3.

The needle guide 13 may have, as in the first embodiment, a mechanism having a degree of freedom such as those shown in FIGS. 10A to 10C, FIGS. 11A to 11C, and FIGS. 12A to 12C so that the direction of puncture can be changed freely.

Although the markers 30 are disposed on the base 15 as shown in FIG. 6 in this embodiment, the present invention is not limited to this, and the markers 30 may be disposed on the first rotational element 11 or the second rotational element 12. In this case, it may be necessary to detect the angle of each rotational element, and to record the position of each marker 30 in the coordinate system of the support device. In other embodiments the markers may be used, for example, for identifying kinds of needle, diameter, cryo-, radio, datum height of needle insertion, etc.

In this embodiment, the rotational elements 11 and 12 and the drive sources 7a and 7b are connected by transmission mechanisms. The transmission mechanisms can be constructed by using, for example, gears or a timing belt.

The medical support device is designed to be placed on a patient. Thus in in use in some embodiments, the first needle-like instrument is guided by the needle guide and is inserted into the body of a patient at a pre-determined angle and having a predetermined first puncture starting point where it punctures the patient's skin.

In one example of an embodiment of the invention, the medical support device is placed on a patient above the patient's liver. An MRI image is obtained while the medical support device is affixed to the patient. An insertion trajectory is planned using the initial MRI image. The planning may include, for example, selecting different locations in a liver lesion for radio frequency ablation by touching the position points on a touch screen showing the MRI image.

The coordinate conversion unit converts these positions on the image into target positions in the coordinate system. The angle calculation unit 2 then calculates combinations of target angles of the two rotational elements that provide correct needle insertion parameters for each the input target positions, and outputs the parameters to an interference analysis unit 3. Then, the medical support device is instructed to move the needle-like instrument guide into the first position. This probe location may be confirmed with an intra-procedural image. The user may then verify the location and insert the needle-like device into the patient's liver. Optionally, the needle-like device may be partially inserted and a confirmation image taken prior to full insertion of the needle-like instrument.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

In referring to the description, specific details are set forth in order to provide a thorough understanding of the examples disclosed. In other instances, well-known methods, procedures, components and circuits have not been described in detail as not to unnecessarily lengthen the present disclosure.

Exemplary embodiments will be described below with reference to the several drawings, wherein like reference numerals designate identical or corresponding parts throughout the several views and embodiments. Accordingly, descriptions of such parts with like reference numerals will not be repeated with respect to multiple figures.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. For example, "about" can mean a range of up to 20% of a given value, and more preferably means a range of up to 10%.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner. It is apparent that variations and modifications of the invention can be made without departing from the spirit or scope of the invention. Upon further study of the specification, further aspects, objects and advantages of this invention will become apparent to those skilled in the art.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto. The scope of the following claims is to be accorded the broadest interpretation so as to encompass all such modifications and equivalent structures and functions.

What is claimed is:

1. A medical support device, comprising:
a first rotational element having a first rotation axis and a first rotational degree of freedom;
a second rotational element having a second rotation axis and a second rotational degree of freedom that is attached to the first rotational element wherein the second rotation axis intersects with the first rotation axis; and
at least one needle guide that is attachable to the second rotational element and is configured to guide the direction of insertion of a needle-like instrument,
wherein the at least one needle guide includes at least one guide portion that guides a first needle-like instrument through a first puncture starting point and guides a second needle-like instrument through a second puncture starting point which is different from the first puncture starting point, wherein,
the at least one needle guide is in a first position when guiding the first needle-like instrument and in a second position when guiding the second needle-like instrument, or
a first needle guide includes a first guide portion that guides a needle-like instrument through the first puncture starting point and a second needle guide includes a second guide portion that guides a needle-like instrument through the second puncture starting point.

2. The medical support device according to claim 1, comprising at least a first needle guide and a second needle guide that simultaneously or sequentially attach to the second rotational element.

3. The medical support device according to claim 2, wherein the first needle guide and second needle guide each have visible or electronic identification markers that distinguish the needle guides.

4. The medical support device according to claim 1, wherein the first puncture starting point and the second puncture starting point are different due to different angles of insertion of the at least one needle guide in the first position and the second position.

5. The medical support device according to claim 1, wherein different location of the first puncture starting point and the second puncture starting point is due to different heights of the at least one needle guide or guides above the plane defined by the first and second puncture starting points in the first position and the second position.

6. The medical support device according to claim 1, further comprising an angle calculation unit configured to determine possible angles of the two rotational elements on the basis of specified target positions and the arrangement of two rotational elements and the at least one needle guide.

7. The medical support device according to claim 6, further comprising an interference analysis unit configured to determine, with respect to the specified different target positions, straight lines showing insertion directions from the possible angles of the two rotational elements with respect to each target position found by the angle calculation unit, and to determine such combinations of insertion directions without interference that the distance between straight lines is greater than or equal to the diameter of the needle-like instrument used.

8. The medical support device according to claim 7, wherein the interference analysis unit selects a combination of insertion directions that is largest in the distance between straight lines or any one combination from the combinations of insertion directions without interference.

9. The medical support device according to claim 7, further comprising a presentation unit configured to present the combinations of insertion directions without interference.

10. The medical support device according to claim 6, wherein the medical support device comprises the two or more needle guides facing in different directions at the same time, and one of the two or more needle guides facing in different directions faces in a direction passing through the intersection of the rotation axes of the two rotational elements, and the others face in such a direction that the distance from the intersection is greater than or equal to the diameter of the needle-like instrument used.

11. The medical support device according to claim 1, wherein the needle guide has a degree of freedom, and the at least one needle guide is configured for changing the direction in which an instrument is guided.

12. The medical support device according to claim 1, wherein the at least one needle guide is configured to release the needle-like instrument after insertion.

13. The medical support device according to claim 1, wherein the two rotational elements each have a position detection unit.

14. The medical support device according to claim 13, wherein at least one of the two rotational elements has a drive unit, and each rotational element is moved to an angle that is found by the angle calculation unit and selected by the interference analysis unit, on the basis of position information obtained by the position detection unit.

15. The medical support device according to claim 1, further comprising a medical imaging machine, and at least three markers that can be imaged by the medical imaging machine.

16. A medical support device, comprising:
at least one rotatable portion having at least one rotational degree of freedom and
at least one needle guide attached to the rotatable portion and having a guide portion, which is configured to:
(a) guide the direction of insertion of a needle-like instrument and
(b) separate from the needle-like instrument after insertion of the needle-like instrument,
wherein the guide portion, when the needle guide is positioned in a first position, is configured to guide the needle-like instrument to a first puncture starting point
wherein the guide portion, when the needle guide is positioned in a second position, or wherein the guide portion of a second needle guide is configured to guide the needle-like instrument to a second puncture starting point which is different from the first puncture starting point.

17. The medical support device according to claim 16, wherein the guide portion is configured to separate from the needle-like instrument via movement out of a notch in the guide portion.

18. A method comprising:
attaching a medical support device to a patient, wherein the medical support device comprises a first rotational element, second rotational element, and at least two needle guides,
defining at least a first location and a second location in the patient for therapeutic intervention based on an image data,
attaching a first needle to a first needle guide,
attaching the first needle guide to the medical support device,
instructing the medical support device to rotate the first rotational element and the second rotational element to a position defined by the first location for therapeutic intervention,
inserting the first needle into the patient,
releasing the first needle from the medical support device,
attaching a second needle to a second needle guide and attaching the second needle guide to the medical support device,
instructing the medical support device to rotate the first rotational element and the second rotational element to a position defined by the second location for therapeutic intervention,
inserting the second needle into the patient, wherein the second needle does not contact the first needle during insertion into the patient, and
releasing the second needle from the medical support device.

* * * * *